United States Patent [19]
Nakagawa et al.

[11] Patent Number: 5,407,930
[45] Date of Patent: * Apr. 18, 1995

[54] CEPHALOSPORIN DERIVATIVES

[75] Inventors: Susumu Nakagawa; Ryuji Mitomo; Ryosuke Ushijima; Akira Asai; Satoru Kuroyanagi, all of Okazaki, Japan

[73] Assignee: Banyu Pharmaceutical Co., Ltd., Tokyo, Japan

[*] Notice: The portion of the term of this patent subsequent to Apr. 4, 2012 has been disclaimed.

[21] Appl. No.: 217,023

[22] Filed: Mar. 24, 1994

Related U.S. Application Data

[63] Continuation of Ser. No. 24,838, Mar. 1, 1993, abandoned, which is a continuation of Ser. No. 720,855, Jul. 15, 1991, abandoned, which is a continuation-in-part of Ser. No. 476,439, Jun. 7, 1990, Pat. No. 5,403,835, which is a continuation-in-part of Ser. No. 28,576, Mar. 20, 1987, Pat. No. 4,880,797.

[30] Foreign Application Priority Data

Mar. 20, 1986 [JP] Japan .................................. 61-60500
Mar. 9, 1987 [JP] Japan .................................. 62-53846

[51] Int. Cl.⁶ .................. C07D 501/46; A61K 31/545
[52] U.S. Cl. ..................................... 514/206; 540/226; 540/227
[58] Field of Search ................. 514/206; 540/227, 226

[56] References Cited
U.S. PATENT DOCUMENTS
4,880,797 11/1989 Nakagawa et al. ................. 514/206

FOREIGN PATENT DOCUMENTS
0238061 9/1987 European Pat. Off. .
0271916 6/1988 European Pat. Off. .
6485 1/1989 Japan .

*Primary Examiner*—Nicholas Rizzo
*Attorney, Agent, or Firm*—Oblon, Spivak, McClelland, Maier & Neustadt

[57] ABSTRACT

The present invention relates to a compound represented by the structural formula I:

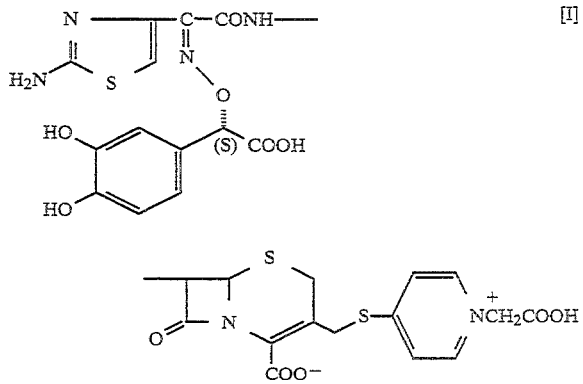

its pharmaceutically acceptable salt or ester, or its crystalline, which is a novel optically active compound useful as a curing agent for bacterial infections, a process for production thereof and a use thereof.

7 Claims, No Drawings

CEPHALOSPORIN DERIVATIVES

This application is a continuation of application Ser. No. 08/024,838, filed Mar. 1, 1993 now abandoned; which is a continuation of application Ser. No. 07/720,855, filed Jun. 15, 1991 now abandoned; which is a Continuation-in-Part of application Ser. No. 07/476,439, filed Jun. 7, 1990, now U.S. Pat. No. 5,403,835, which is a Continuation-in-Part of application Ser. No. 07/028,576, filed Mar. 20, 1987, now U.S. Pat. No. 4,880,797; which were filed as International Application Nos. PCT/JP90/01472 on Nov. 13, 1990 PCT/JP89/0155 on Nov. 13, 1989.

TECHNICAL FIELD

The present invention relates to a cephem compound useful as a curing agent for bacterial infections in the field of medicine, particularly, optically active 7-[(Z)-2-(2-aminothiazol-4-yl)-2-[[(S)-α-carboxy-3,4-dihydroxybenzyl]oxyimino]acetamido]-3-[(1-carboxymethyl-4-pyridinio)thiomethyl]-3-cephem-4-carboxylate, its pharmaceutically acceptable salt or ester, or its crystalline, a process for the production thereof and a use thereof.

BACKGROUND TECHNOLOGY

The present inventors have found that 7-[(Z)-2-(2-aminothiazol-4-yl)-2-[(α-carboxy-3,4-dihydroxybenzyl)oxyimino]acetamido]-3-[(1-carboxymethyl-4-pyridinio)thiomethyl]-3-cephem-4-carboxylate (hereinafter referred to simply as BO-1463) has good antibacterial activities against Gram-positive bacteria and Gram-negative bacteria, and have filed a U.S. patent application (Ser. No. 07/028,576 now 4880796) concerning BO-1463. BO-1463 is a cephem compound expected to practically be used as a curing agent for bacterial infections.

However, the description of the specification of the U.S. Patent Application refers nothing about optically active compounds based on the asymmetric carbon of a (α-carboxy-3,4-dihydroxybenzyl)oxyimino group substituting at the acyl side chain, and such optically active compounds or their crystalline have not been synthesized.

β-lactam antibiotics exhibit selective toxicity against bacteria only and present no substantial effects against animal cells, and they have been widely used for the treatment of infectious diseases caused by bacteria as antibiotics having no substantial side effects. Thus, they are highly useful drugs.

However, in recent years, glucose non-fermentative Gram-negative rods, particularly *Pseudomonas aeruginosa* have been frequently isolated from immuno-compromised patients, as causative organisms of refractory infections and have posed various problems. Therefore, it has been desired to develop an antibacterial agent having an improved activity against such bacteria.

DISCLOSURE OF INVENTION

It is an object of the present invention to provide novel cephalosporin derivatives having excellent antibacterial activities, and the present inventors have conducted extensive researches concerning novel cephalosporin derivatives having a 1-carboxymethylpyridinio-4-ylthiomethyl group at the 3-position of the cephem nucleus and a 2-(2-aminothiazol-4-yl)-2-(substituted oxyimino)acetamide group at the 7-position of the cephem nucleus. As a result, acylation was conducted by using (Z)-2-(2-aminothiazol-4-yl)-2-[[(S)-α-carboxy-3,4-dihydroxybenzyl]oxyimino]acetic acid derivative wherein the asymmetric carbon of the (α-carboxy-3,4-dihydroxybenzyl)oxyimino group substituting at the acyl side chain took S-configuration, to synthesize the S-isomer of amorphous BO-1463 which was the compound of the present invention, i.e. 7-[(Z)-2-(2-aminothiazol-4-yl)-2-[[(S)-α-carboxy-3,4-dihydroxybenzyl]oxyimino]acetamido]-3-[(1-carboxymethyl-4-pyridinio)-thiomethyl]-3-cephem-4-carboxylate (hereinafter referred to simply as BO-1463S). The present inventors have found that amorphous BO-1463S has antibacterial activities apparently superior to amorphous BO-1463 which is the racemic compound and the R-isomer (hereinafter referred to simply as BO-1463R); that crystalline BO-1463S and its solvate have excellent stability, which are obtained by crystallizing using, as the starting material, amorphous BO-1463S which has been desired to be improved with respect to the stability, followed by isolation and purification; and that they are further useful as a medicine used for the treatment and prevention of human infectious diseases. The present invention has been accomplished on the basis of such discoveries.

The present invention relates to a compound represented by the structural formula I:

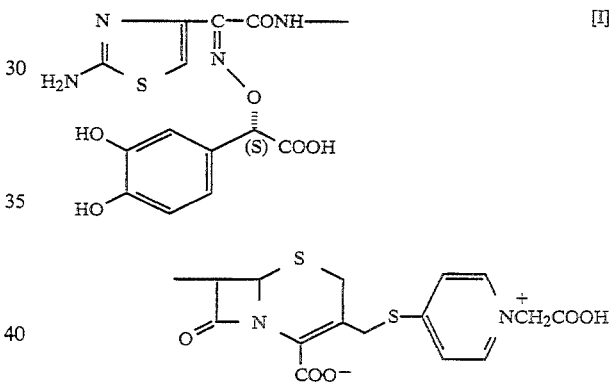

[I]

its pharmaceutically acceptable salt or ester, or its crystalline which is a novel optically active compound useful as a curing agent for bacterial infections, a process for production thereof and a use thereof.

Now, the symbols and terms used in the present description will be explained.

Each of $R^1$, $R^2$ and $R^4$ is a hydrogen atom or a carboxyl-protecting group selected from the group consisting of a benzhydryl group, a tert-butyl group and a p-methoxybenzyl group, particularly preferably a benzhydryl group or a p-methoxybenzyl group.

$R^3$ is a hydrogen atom or an amino-protecting group selected from the group consisting of a trityl group, a formyl group and a tert-butoxycarbonyl group, particularly preferably a trityl group.

X is a halogen atom, for example, a chlorine atom, a bromine atom, an iodine atom or the like, particularly preferably a chlorine atom or an iodine atom.

$X^-$ is an anion, for example, a chloride ion, a bromide ion, an iodide ion, a sulfate ion, a nitrate ion, a phosphate ion, a perchlorate ion or the like, particularly preferably a chloride ion or an iodide ion.

In the structural formula I, formulas III, IV and VI, all the asymmetric carbons take S-configuration.

The partial structure

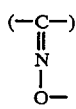

in the oxyimino group of the structural formula I has a syn-isomer (Z-configuration:

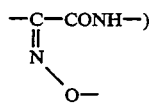

and an anti-isomer (E-configuration:

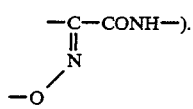

Generally, the syn-isomer exhibits excellent antibacterial activities, and all the oxyimino groups in this description are syn-isomers. The E-Z nomenclature is disclosed in *J. Am. Chem. Soc.*, vol. 90, p. 509 (1968).

The salt of the compound of the structural formula I means pharmaceutically acceptable one known to be commonly used, and a salt at the carboxyl group at the 4-position of the cephem nucleus or the carboxyl group substituting at the 3-position side chain or the 7-position acyl side chain, or a salt at the base of the 2-aminothiazolyl group substituting at the acyl side chain and the like, may be mentioned.

As a basic addition salt at the carboxyl group, for example, a salt of an alkali metal such as sodium or potassium; a salt of an alkaline earth metal such as calcium or magnesium; a salt of ammonium; a salt of an aliphatic amine such as trimethylamine, triethylamine, dicyclohexylamine, ethanolamine, diethanolamine, triethanolamine, tromethamine, glucamine, N-methylglucamine or procaine; a salt of an aralkylamine such as N,N'-dibenzylethylenediamine; a salt of a heterocyclic aromatic amine such as pyridine, picoline, quinoline or isoquinoline; a salt of a quaternary ammonium such as tetramethylammonium, tetraethylammonium, benzyltrimethylammonium, benzyltriethylammonium, benzyltributylammonium, methyltrioctylammonium or tetrabutylammonium; and a salt of a basic amino acid such as arginine or lysine, may be mentioned.

As an acid addition salt at the base of the 2-aminothiazolyl group, for example, a salt of an inorganic acid such as hydrochloric acid, sulfuric acid, nitric acid, phosphoric acid, carbonic acid, hydrogencarbonic acid or perchloric acid; a salt of an organic acid such as formic acid, acetic acid, propionic acid, lactic acid, maleic acid, fumaric acid, tartaric acid, malic acid, citric acid or ascorbic acid; a salt of a sulfonic acid such as methanesulfonic acid, isethionic acid, benzenesulfonic acid or p-toluenesulfonic acid; and a salt of an acidic amino acid such as aspartic acid or glutamic acid, may be mentioned.

The non-toxic ester of the compound of the structural formula I means pharmaceutically acceptable commonly one at the carboxyl group at the 4-position of the cephem nucleus or the carboxyl group substituting at the side chain at the 3-position or at the acyl side chain at the 7-position of the cephem nucleus. For example, an ester with an alkanoyloxymethyl group such as acetoxymethyl group or a pivaloyloxymethyl group, an ester with an alkoxycarbonyloxyalkyl group such as a 1-(ethoxycarbonyloxy)ethyl group, an ester with a phthalidyl group, and an ester with a (5-substituted-2-oxo-1,3-dioxol-4-yl)methyl group such as a (5-methyl-2-oxo-1,3-dioxol-4-yl)methyl group, may be mentioned.

Particularly, when an ester is formed at the carboxyl group of the cephem nucleus, the above-mentioned anion which is added from outside is necessary.

The crystalline solvate of the compound of the structural formula I means a solvate of the compound of the structural formula I (BO-1463) and a suitable solvent. Preferred solvents are, for example, water, a lower aliphatic alcohol such as methanol, ethanol or propanol, a lower aliphatic carboxylic acid such as formic acid or acetic acid and an inert solvent such as N,N-dimethylformamide, dimethylacetamide, N-methylpyrrolidone, acetonitrile or tetrahydrofuran, and water and formic acid are particularly preferred.

First of all, the process for producing the compound of the structural formula I of the present invention which is useful as the starting material for crystalline BO-1463S and its solvate, will be explained.

The compound of the structural formula I is produced by reacting a compound of the formula II:

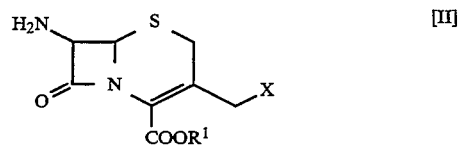

wherein $R^1$ is a hydrogen atom or a carboxyl-protecting group selected from the group consisting of a benzhydryl group, a tert-butyl group and a p-methoxybenzyl group, and X is a halogen atom; or its salt, with a compound of the formula III:

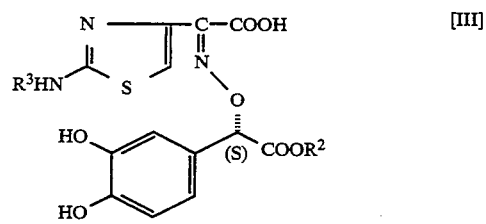

wherein $R^2$ is a hydrogen atom or a carboxyl-protecting group selected from the group consisting of a benzhydryl group, a tert-butyl group and a p-methoxybenzyl group, and $R^3$ is a hydrogen atom or an amino-protecting group selected from the group consisting of a trityl group, a formyl group and a tert-butoxycarbonyl group; or a reactive derivative to derive a compound of the formula IV:

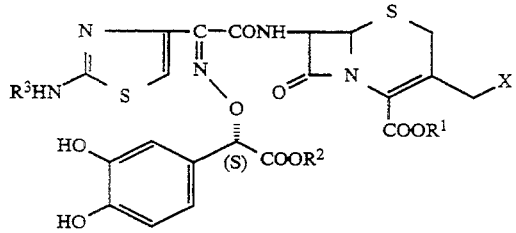

wherein $R^1$, $R^2$, $R^3$ and X are as defined above; or its salt, reacting the compound or its salt with a compound of the formula V:

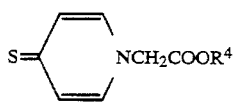

wherein $R^4$ is a hydrogen atom or a carboxyl-protecting group selected from the group consisting of a benzhydryl group, a tert-butyl group and a p-methoxybenzyl group to obtain a compound of the formula VI:

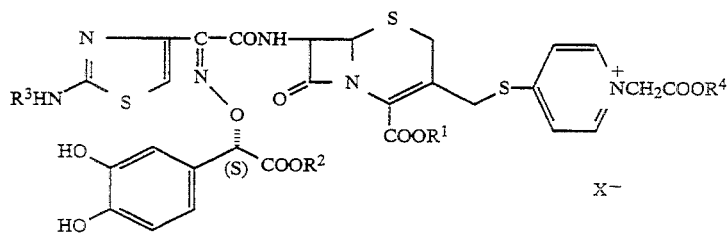

wherein $R^1$, $R^2$, $R^3$ and $R^4$ are as defined above, and $X^-$ is an union, and optionally removing the protecting groups of the compound of the formula VI.

The process for producing the compound of the structural formula I of the present invention will be explained in further detail.

The compound of the formula IV is produced by reacting the compound of the formula II with the carboxylic acid of the formula III or its reactive derivative (e.g. an acid halide, a mixed acid anhydride, an active ester or the like) in an inert solvent which does not adversely affect the reaction, such as water, acetone, dioxane, acetonitrile, tetrahydrofuran, methylene chloride, chloroform, ethylene chloride, benzene, ethyl acetate, N,N-dimethylformamide or dimethyl sulfoxide, or in a mixed solvent thereof.

In the acylation, the molar number of a reactive reagent, the reaction temperature and the reaction time vary depending upon the type of the carboxylic acid of the formula III or its reactive derivative, but the acylation is usually completed by using from 1 to 1.5 mols of the carboxylic acid of the formula III or its reactive derivative relative to one mol of the compound of the formula II at a temperature of from $-40°$ to $40°$ C. for from 0.5 to 2 hours.

When an acid halide is used as the reactive derivative of the formula III, the acylation reaction is preferably conducted in the presence of from 1 to 2 mols of a base such as triethylamine, N,N-diisopropylethylamine, N-methylmorpholine, N,N-dimethylaniline or pyridine, relative to one mol of the acid halide.

The acid halide-forming reaction is completed by reacting the carboxylic acid of the formula III with from 1 to 10 mols, preferably from 1 to 1.5 mols of a halogenating agent such as thionyl chloride, phosphorus trichloride, phosphorus tribromide, phosphorus pentachloride, phosphorus oxychloride, oxalyl chloride or phosgene, relative to one mol of the carboxylic acid of the formula III in an inert solvent which does not adversely affect the reaction, such as acetone, dioxane, acetonitrile, tetrahydrofuran, methylene chloride, chloroform, ethylene chloride, benzene, ethyl acetate, N,N-dimethylformamide or dimethyl sulfoxide, or in a mixed solvent thereof at a temperature of from $-40°$ to $100°$ C., preferably from $-20°$ to $20°$ C. for from 10 to 120 minutes.

The mixed acid anhydride-forming reaction is completed by reacting the carboxylic acid of the formula III with from 1 to 1.2 mols of a chloroformate such as methylchloroformate, ethylchloroformate or isobutylchloroformate relative to one mol of the carboxylic acid of the formula III in an inert solvent which does not adversely affect the reaction, such as acetone, dioxane, acetonitrile, tetrahydrofuran, methylene chloride, chloroform, ethylene chloride, benzene, ethyl acetate, N,N-dimethylformamide or dimethyl sulfoxide, or in a mixed solvent thereof in the presence of from 1 to 1.2 mols of a base such as triethylamine, N,N-diisopropylethylamine, N-methylmorpholine, N,N-dimethylaniline or pyridine at a temperature of from $-40°$ to $20°$ C., preferably from $-20°$ to $5°$ C. for from 10 to 60 minutes.

The active ester-forming reaction is completed by reacting the carboxylic acid of the formula III with from 1 to 1.2 mols of an N-hydroxy compound such as N-hydroxysuccinimide or 1-hydroxybenzotriazole, or a phenol compound such as 4-nitrophenol, 2,4-dinitrophenol or 2,4,5-trichlorophenol, and from 1 to 1.4 mols of a condensing agent such as N,N'-dicyclohexylcarbodiimide, relative to one mol of the carboxylic acid of the formula III in an inert solvent which does not adversely affect the reaction, such as acetone, dioxane, acetonitrile, tetrahydrofuran, methylene chloride, chloroform, ethylene chloride, benzene, ethyl acetate, N,N-dimethylformamide or dimethyl sulfoxide or in a mixed solvent thereof at a temperature of from $-10°$ to $50°$ C. for from 0.5 to 2 hours.

The compound of the formula IV is also produced by reacting the compound of the formula III with the compound of the formula II in the above-mentioned inert solvent which does not adversely affect the reaction, or by the direct action of a condensing agent in the absence of a solvent. As the condensing agent, for example, a carbodiimide such as N,N'-dicyclohexylcarbodiimide; phosphorus oxychloride or an adduct of N,N-dimethylformamide-phosphorus oxychloride (Vilsmeier reagent), may be mentioned. However, when phosphorus oxychloride or its adduct is used, a base such as triethylamine, N,N-diisopropylethylamine, N-methylmorpholine, N,N-dimethylaniline or pyridine, is necessary.

In such condensation reactions, from 1 to 1.5 mols of the compound of the formula III and from 1 to 2 mols of the condensing agent (when conducted in the above mentioned inert solvent) are used relative to one mol of the compound of the formula II. The reaction temperature and the reaction time vary depending upon the type of the condensing agent to be used, but the reaction is usually completed at a temperature of from −20° to 20° C. for from 0.5 to 3 hours. Particularly, as the condensing agent, phosphorus oxychloride is preferred. As a preferred example of the reaction, from 1.5 to 3 mols, preferably from 2 to 2.5 mols of phosphorus oxychloride, relative to one mol of the compound of the formula II and from 1 to 1.5 mols of the compound of the formula III is operated in an inert solvent which does not adversely affect the reaction, such as acetone, dioxane, acetonitrile, tetrahydrofuran, methylene chloride, chloroform, ethylene chloride, benzene, ethyl acetate, N,N-dimethylformamide or dimethyl sulfoxide in the presence of from 1 to 2 mols, preferably 1.5 mols of a base such as triethylamine, N,N-diisopropylethylamine, N-methylmorpholine, N,N-dimethylaniline or pyridine at a temperature of from −20° to 0° C. for from 10 to 20 minutes, and the reaction is conducted by an addition of further from 1.2 to 2 mols, preferably 1.5 mols of the above mentioned base to the reaction solution at a temperature of from −10° to 10° C. for from 1 to 2 hours to obtain the compound of the formula IV.

The compound of the formula VI is produced by reacting the compound of the formula IV with the 4-pyridothione derivative of the formula V in an inert solvent which does not adversely affect the reaction, such as methylene chloride, chloroform, diethyl ether, ethyl acetate, butyl acetate, tetrahydrofuran, acetonitrile, N,N-dimethylformamide or dimethyl sulfoxide, or in a mixed solvent thereof in the presence or absence of a base.

As the base, for example, a salt of a metal such as sodium carbonate, potassium carbonate or magnesium carbonate, and an organic amine such as triethylamine, N,N-diisopropylethylamine, N-methylmorpholine or N,N-dimethylaniline, may be mentioned.

When $R^4$ in the formula V is a hydrogen atom, the compound of the formula V may be used as a salt of a metal such as sodium, potassium, calcium, magnesium or silver, or a salt of an organic amine such as triethylamine or ethyldiisopropylamine. Further, the compound of the formula V can be used after silylation by a silylating agent such as N,O-bis(trimethylsilyl)-acetamide.

The reaction is completed by reacting 1 mol of the compound of the formula IV with from 1 to 2 mols of the compound of the formula V at a temperature of from 0° to 40° C. for from 0.5 to 5 hours.

The compound of the structural formula I of the present invention can optionally be produced by removing the protecting groups from the compound of the formula VI.

The removal of the protecting groups for a carboxyl group or an amino group in the formula VI is conducted by using a method to be commonly used in the field of the synthesis of β-lactam by optional selection. The methods of introducing and removing a protecting group are conducted in accordance with a method disclosed in e.g. "Protective Groups in Organic Synthesis", written by T. W. Greene, published by Wiley (1981), "Protective Groups in Organic Chemistry", written by J. F. W. McOmie, published by Plenum Press (1973) or the like.

The removal of a protecting group such as a trityl group, a formyl group, a tert-butoxycarbonyl group or a benzhydryl group can be conducted by using an inorganic acid or an organic acid such as hydrochloric acid, formic acid, trifluoroacetic acid, benzenesulfonic acid or p-toluenesulfonic acid in the presence or absence of a solvent. Particularly, trifluoroacetic acid is preferred. When trifluoroacetic acid is used as the acid, the reaction is facilitated by an addition of, for example, anisole, thioanisole, phenol or the like, and the side reaction is also controlled.

The reaction of removing a protecting group is usually conducted in a solvent which does not adversely affect the reaction, such as water, methylene chloride, chloroform, ethylene chloride, benzene, or in a mixed solvent thereof. The reaction temperature and the reaction time are optionally selected depending upon the chemical properties of the compound VI and the compound I of the present invention, and the type of protecting group, and the reaction is usually completed by treating the compound VI at a temperature of from −20° to 20° C. for from 0.5 to 3 hours.

After completion of the reaction of removing the protecting group, the compound represented by the structural formula I of the present invention and its pharmaceutically acceptable salt or ester can be isolated by a usual treatment method such as column chromatography by using silica gel or an adsorption resin, freeze drying or crystallization.

Further, the salt or ester of the compound of the structural formula I can readily be derived from the compound of the structural formula I by a usual method.

Secondly, crystalline BO-1463S and its solvate, and their processes are described in detail.

Crystalline BO-1463S and its solvate which are the desired products of the present invention are produced by stirring a powder or crude of amorphous BO-1463S in a solvent selected from the group consisting of water, a hydrophilic organic solvent and a mixture thereof at a temperature range of from −20° to 60° C., preferably from 0 to 40° C. and collecting the precipitated crystal. As the case required, an inorganic acid such as hydrochloric acid, sulfuric acid or phosphoric acid; an organic acid such as formic acid or acetic acid is added to the solution to adjust the pH to be not more than 4.0. Further, crystallization can be promoted by having a crystalline substance co-existed as seed.

As the powder or crude of amorphous BO-1463S, a free form of BO-1463S, its basic salt, its acid addition salt, its non-toxic ester and their solvates may be mentioned.

As the preferred solvent, water, a lower aliphatic alcohol such as methanol, ethanol, propanol, isopropanol or butanol; a lower aliphatic carboxylic acid such as formic acid or acetic acid; an inert organic solvent such as N,N-dimethylformamide, dimethylacetamide, N-methylpyrrolidone, acetonitrile or tetrahydrofuran and a solvent mixture of the above organic solvent and water may be mentioned. Water and formic acid are particularly preferred. In the solvent mixture of the above organic solvent and water, water can be contained in an amount of from 10% to 90%.

After collecting the precipitated crystal by filtration, the crystal is dried under a suitable condition such as air-drying at from 5° to 25° C. or vacuum drying at −20° to 25° C., whereby crystalline BO-1463S and its solvate can be produced. Further, recrystallization can be conducted in a usual method by using a suitable acidic solvent.

Crystalline BO-1463S can be obtained in a form of an ester, a basic salt, an acidic salt, etc. depending on the starting material of the amorphous BO-1463S. Further, by selecting a suitable solvent and using a conventional method, various solvates thereof can be produced.

For example, a hydrate of BO-1463S can be produced efficiently by adding water.

Particularly, as the starting material, a free form and an alkali metal salt such as disodium salt of amorphous BO-1463S are preferred.

The compound of the formula IV wherein X is an iodine atom is produced by reacting the compound of the formula IV wherein X is a chlorine atom with an iodide such as sodium iodide or potassium iodide, in accordance with a method disclosed in e.g. Japanese Examined Patent Publication No. 27679/1976 and *Synth. Commun.*, vol. 16, p. 1029–1035 (1986), in a solvent such as acetone, N,N-dimethylformamide or dimethyl sulfoxide, or in a two-phase system of water and an organic solvent in the presence of a phase transfer catalyst, at from freezing point to room temperature, and it is used to a subsequent reaction after isolation or without isolation.

The compound of the formula IV is obtained by reacting the compound of the formula II derived from e.g. 7-aminocephalosporanic acid, a 7-acylamino-3-halomethyl-3-cephem-4-carboxylate derivative (produced in accordance with Japanese Unexamined Patent Publication No. 72590/1983 or No. 154588/1983) or known 7-acylaminocephalosporanic acid by a usual method, with the compound of the formula III.

The 2-(2-aminothiazol-4-yl)-2-[[(S)-α-carboxy-3,4-dihydroxybenzyl]oxyimino]acetic acid derivative of the formula III is produced by using a 2-(2-aminothiazol-4-yl)glyoxylic acid derivative or a 2-(2-aminothiazol-4-yl)-2-(hydroxyimino)acetic acid derivative in accordance with a method disclosed in *Chem. Pharm. Bull.*, vol. 25, p. 3115–3119 (1977), Nihon Kagaku Kaishi, p. 785–801 (1981) or the like.

The 1-benzhydryloxycarbonylmethyl-4-pyridothione represented by the formula V is produced in accordance with a method disclosed in *J. Chem. Soc.*, p. 3610 (1958). For example, it is produced by reacting benzhydryl α-chloroacetate with 4-hydroxypyridine in a solvent of N,N-dimethylformamide in the presence of potassium carbonate at a temperature of from 40° to 80° C. to obtain 1-benzhydryloxycarbonylmethyl-4-pyridone, followed by reacting phosphorus pentasulfide with the compound thereby obtained in a solvent of tetrahydrofuran at a temperature of from 40° to 80° C.

The in vitro antibacterial activities of the amorphous BO-1463S of the present invention against various bacteria, were measured by the following agar plate dilution method [Nihon Kagaku Ryoho Gakkai Standard Method: Chemotherapy, vol. 29, p. 76–79 (1981)]. One platinum loopful of each test bacterial strain incubated over night in Mueller Hinton broth, was inoculated to Mueller Hinton agar (inoculum size: $10^6$ CFU/ml). Such culture media containing various antibiotics in various concentrations were prepared. After incubation at 37° C. for 16 hours, the minimum inhibitory concentrations (MIC: μg/ml) were measured. The results are shown in Table below.

Now, the following compounds were used as comparative compounds.

BO-1463 (The compound disclosed in Example 5 of U.S. patent application Ser. No. 07/028,576 now 4,880,797): Disodium 7-[(Z)-2-(2-aminothiazol-4-yl)-2-[(α-carboxylato-3,4-dihydroxybenzyl)oxyimino]acetamido]-3-[(1-carboxylatomethyl-4-pyridinio)thiomethyl]-3-cephem-4-carboxylate BO-1463R: Disodium 7-[(Z)-2-(2-aminothiazol-4-yl)-2-[(R)-α-carboxylato-3,4-dihydroxybenzyl]oxyimino]acetamido]-3-[(1-carboxylatomethyl-4-pyridinio)thiomethyl]-3-cephem-4-carboxylate (the compound of Reference Example 13) cefotaxime ceftazidime

|  | MIC (μg/ml, $10^6$ CFU/ml, MH agar) | | | | |
|---|---|---|---|---|---|
|  | Test compound | | | | |
| Test microorganisms | BO-1463S | BO-1463 | BO-1463R | ceftazidime | cefotaxime |
| *E. coli* NIHJ JC2 | 0.1 | 0.2 | 0.39 | 0.2 | 0.05 |
| *E. coli* CSH2 (RK1)* | 0.1 | 0.2 | 0.39 | 0.2 | 0.025 |
| *E. coli* CSH (RE45)* | 0.05 | 0.1 | 0.2 | 0.1 | 0.2 |
| *K. oxytoca* GN10650* | 0.1 | 0.2 | 0.39 | 0.2 | 0.78 |
| *E. cloacae* Nek 39* | 0.78 | 1.56 | 12.5 | 3.13 | 6.25 |
| *E. coli* GN5482* | 0.39 | 0.78 | 1.56 | 3.13 | 0.78 |
| *S. marcescens* NO. 16-2* | 3.13 | 6.25 | 50 | 3.13 | 25 |
| *Ps. aeruginosa* IFO3445 | 0.39 | 0.78 | 12.5 | 0.78 | 3.13 |
| *Ps. aeruginosa* AK 109 | 0.1 | 0.2 | 25 | 1.56 | 12.5 |
| *Ps. aeruginosa* AKR17 | 0.39 | 1.56 | >100 | >100 | >100 |
| *Ps. cepacia* 23 | 0.05 | 0.1 | 0.2 | 1.56 | 6.25 |
| *A. calcoaceicus* No. 4 | 0.2 | 0.39 | 0.39 | 3.13 | 12.5 |
| Geometric mean value of all microorganisms | 0.482 | 1.03 | 25.29 | 17.96 | 22.29 |

*β-lactamase-producing bacteria

It being provided that calculations were conducted as >100 being 200.

The compound of the present invention has evidently superior antibacterial activities against intestinal bacteria group such as genus Enterococcus, genus Klebsiella, genus Proteus, genus Serratia and genus Enterobacter, and glucose non-fermentative Gram-negative rods of genus Pseudomonas which are clinically problematic, to BO-1463 which is a racemic compound of the compound of the present invention, and BO-1463R (Reference Example 13) which is a diastereomer of the compound of the present invention.

TEST EXAMPLE 1: Stability test

Stability tests of the crystalline compounds of the present invention were conducted by using crystals obtained in Examples 2 and 4 as representative compounds, and by using an amorphous powder (compound of Example 1) as comparative compound.

10 mg of crystalline powders and an amorphous powder were sealed in vials and preserved at 60° C., respectively. After one day, three days and five days from the initiation of the preservation, the remaining rate (%) of the compounds to be measured were measured by high performance liquid chromatography (HPLC). The results thus obtained are shown in the following Table.

| Compound to be measured | Remaining rate (%) | | |
|---|---|---|---|
| | 1 Day | 3 Days | 5 Days |
| Crystalline formic acid solvate (compound of Example 2) | 98.4 | 97.6 | 89.2 |
| Crystalline hydrate (compound of Example 4) | 98.2 | 97.9 | 89.7 |
| Amorphous powder (compound of Example 1) | 80.5 | — | 58.9 |

Accordingly, the compound of the structural formula I and its pharmaceutically acceptable salt or ester of the present invention are useful as medicine for treatment and prevention of human infectious diseases.

The compounds of the present invention may be mixed with a carrier of solid or liquid excipient which has been known in this field, and may be used in the form of a pharmaceutical formulation suitable for parenteral administration, oral administration or external administration.

As the pharmaceutical formulations, there may be mentioned liquid formulations such as injection solutions, syrups and emulsions, solid formulations such as tablets, capsules and granules and formulations for external application such as ointments and suppositories. Further, these formulations may contain additives which are commonly employed such as bases, assisting agents, stabilizers, wetting agents, emulsifying agents, absorption-promoting agents or surfactants.

As such additives, distilled water for injection, a Ringer's solution, glucose, sucrose syrup, gelatin, edible oil, cacao butter, ethylene glycol, sucrose, corn starch, magnesium stearate and talc, may be mentioned.

The compound of the present invention can be used as an antibacterial agent for the treatment of human infectious diseases caused by Gram-positive bacteria and Gram-negative bacteria including glucose non-fermentative Gram-negative rods such as *Pseudomonas aeruginosa*. The dose may be varied depending upon the conditions of the patient such as the age and the sex, and is usually within a range of from 1 to 100 mg/kg per day. It is preferred to administer a daily dose of from 5 to 30 mg/kg in 2 to 4 times.

Now, the present invention will be described in further detail with reference to Examples and Reference Examples. However, it should be understood that the present invention is by no means restricted to these specific Examples.

EXAMPLE 1

Disodium 7-[(Z)-2-(2-aminothiazol-4-yl)-2-[[(S)-α-carboxylato-3,4-dihydroxybenzyl]oxyimino]acetamido]-3-[(1-carboxylatomethyl-4-pyridinio)thiomethyl]-3-cephem-4-carboxylate (A) 60.5 g (0.0794 mol) of (Z)-2-[[(S)-α-benzhydryloxycarbonyl-3,4-dihydroxybenzyl]oxyimino]-2-(2-tritylaminothiazol-4-yl)acetic acid and 32.2 g (0.0794 mol) of p-methoxybenzyl 7-amino-3-chloromethyl-3-cephem-4-carboxylate were suspended in 600 ml of tetrahydrofuran, and 22.1 ml (0.158 mol) of triethylamine was added thereto at −5° C. The mixture was stirred at the same temperature for 30 minutes. Then, 18.5 ml (0.198 mol) of phosphorus oxychloride was dropwise added thereto at a temperature of from −10° to −5° C. over a period of 15 minutes. After stirring for 10 minutes, 27.6 ml (0.198 mol) of triethylamine was added thereto at a temperature of at most −5° C., and the mixture was stirred at a temperature of at most 5° C. for 1.5 hours. The reaction mixture was added to a mixed solution of 500 ml of water and 300 ml of ethyl acetate and subjected to liquid separation. The aqueous layer was further extracted with 100 ml of ethyl acetate, and the extract was put together with the organic layer. 120 ml of a saturated sodium hydrogencarbonate aqueous solution was gradually added to the organic layer, and the mixture was stirred for one hour. Then, the organic layer was washed with 400 ml of a saturated sodium chloride aqueous solution, dried over anhydrous magnesium sulfate and concentrated under reduced pressure to obtain a foam-like solid. The foam-like solid thereby obtained was subjected to silica gel column chromatography (Wakogel® C-300, hexane/ethyl acetate =10/3→10/9). The desired fractions were put together and concentrated under reduced pressure to obtain 44.0 g (yield: 50%) of p-methoxybenzyl 7-[(Z)-2-[[(S)-α-benzhydryloxycarbonyl-3,4-dihydroxybenzyl]oxyimino]-2-(tritylaminothiazol-4-yl)acetamido]-3-chloromethyl-3-cephem-4-carboxylate as a foam-like solid.

IR(KBr)cm$^1$: 3375, 1790, 1730, 1680, 1510, 1250, 1175, 700 NMR (CDCl$_3$) δ: 3.38 and 3.57(2H,ABq,J=18 Hz), 3.83(3H,s), 4.43 and 4.62(2H,ABq,J =12 Hz), 4.99(1H,d,J =5 Hz), 5.18 and 5.33(2H,ABq,J =12 Hz), 5,89(1H,s), 6.08(1H,dd,J =5&8 Hz), 6,73(1H,s), 6.8-7.6(37H,m), 8.42(1H,d,J =8 Hz)

(B) 33.38 g (30 mmol) of the compound obtained in the above reaction (A) was dissolved in 270 ml of N,N-dimethylformamide, and the mixture was cooled to 5° C. 24.9 g (0.15 mol) of potassium iodide was added thereto, and the mixture was stirred at a temperature of at most 5° C. for one hour. To this reaction mixture, 10.55 g (31 mmol) of 1-benzhydryloxycarbonylmethyl-4-pyridothione was added, and the mixture was stirred at a temperature of at most 5° C. for 3 hours. The reaction solution was added to a mixed solution of 400 ml of ethyl acetate and 270 ml of water, and the organic layer was separated. The organic layer was washed with 240 ml of water and 120 ml of a saturated sodium chloride aqueous solution and dried over anhydrous magnesium sulfate. The organic layer was concentrated under reduced pressure to dryness to obtain 46.2 g (yield: 100%) of p-methoxybenzyl 7-[(Z)-2-[[(S)-α-benzhydryloxycarbonyl-3,4-dihydroxybenzyl]oxyimino]-2-(tritylaminothiazol-4-yl)acetamido]-3-[(1-benzhydryloxycarbonylmethyl-4-pyridinio)thiomethyl]-3-cephem-4-carboxylate iodide as a foam-like solid.

IR (KBr) cm$^1$: 3380, 1785, 1745, 1730, 1630, 1515, 1490, 1245, 1210, 1180, 1105, 700 NMR (CDCl$_3$) δ: 3:3.22 and 3.46(2H,ABq,J =18 Hz), 3.69(3H,S), 4.15 and 4.33(2H,ABq,J =12 Hz), 4.84(1H,d,J =4.5 Hz), 5.15(2H,br s), 5.53(2H,br s), 5.65(1H,dd,J =4.5&8 Hz), 5.81(1H,s), 6.6-7.6(52H,m), 8.09(1H,d,J =8 Hz)

(C) 46.2 g (30 mmol) of the compound obtained in the above reaction (B) was dissolved in 220 ml of methylene chloride, 32.6 ml of anisole was added thereto, and the mixture was cooled to 0° C. A solution of 109 ml of methylene chloride and 347 ml of trifluoroacetic acid which were previously cooled to 0° C., was added thereto, and the mixture was stirred at a temperature of at most 5° C. for 3 hours. The solvent was distilled off under reduced pressure, and 900 ml of diisopropyl ether was added to the residue. The mixture was stirred for one hour and subjected to filtration to obtain 29.2 g of a crude product. This crude product was suspended in 140 ml of water and dissolved by adjusting to pH 6.8 with a 2N sodium hydroxide aqueous solution under cooling with ice. The solution was subjected to reversed phase column chromatography (LC-Sorb®, RP-18, Chemco Co.; eluted by a 5% methanol aqueous solution), and the desired fractions were put together. The solvent was distilled off under reduced pressure, and the residue was freeze-dried to obtain 12.2 g (yield: 54%) of the above identified compound.

Angle of rotation: $[\alpha]_D^{21} -3.1°$ (c 1, water) IR(KBr)cm$^1$: 3400, 1770, 1630, 1600, 1540, 1530, 1380, 1105 NMR (D$_2$O) δ: 3:3.22 and 3.56 (2H, ABq, J=18 Hz), 4.19 and 4.29(2H,ABq,J=12 Hz), 4.99(2H,s), 5.06(1H,d,J=4.5 Hz), 5.42(1H,s), 5.68(1H,d,J=4.5 Hz), 6.86(1H,d,J=8 Hz), 6.93(1H,d,J=8 Hz), 6.95(1H,s), 7.02(1H,s), 7.80(2H,d,J=6 Hz), 8.23(2H,d,J=6 Hz) HPLC: Column: YMC®-Pack A-302 C$_{18}$, 5μ, 4.6φ×150 mm Mobile phase: 0.01M phosphoric acid aqueous solution/methanol (80/20) Flow rate: 1.0 ml/min. Temperature: 40° C. Detection: 280 nm Retention time: 3.52 min.

EXAMPLE 2

Crystal of 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid formic acid solvate 300 mg of disodium 7-[(Z)-2-(2-aminothiazol-4-yl)-2-(S)-α-carboxylato-3,4-dihydroxybenzyl]oxyimino]acetamido]-3-[(1-carboxylatomethyl-4-pyridinio)thiomethyl]-3-cephem-4-carboxylate was added to 1.5 ml of formic acid and stirred at room temperature for 5 minutes to dissolve. After adding 1.8 ml of water to the reaction solution, a seed crystal was added thereto and stirred at room temperature for 1.5 hours. 1.2 ml of water was further added thereto and stirred at room temperature for 1 hour. The precipitated crystal was collected and washed with 2 ml of water and acetone (2 ml×2), followed by air-drying at room temperature for 3 hours, whereby 278 mg of the above-identified crystal was obtained.

Melting point: 201° C. (decomposition) IR(KBr)cm$^1$: 3400, 1770, 1630, 1530, 1380, 1110 NMR(D$_2$O, NaHCO$_3$) δ: 3.21 and 3.56(2H,ABq,J=18 Hz), 4.19 and 4.35(2H,ABq,J=14 Hz), 5.02(2H,s), 5.08(1H,d,J=4.5 Hz), 5.44(1H,s), 5.69(1H,d,J=4.5 Hz), 6.8-7.1(4H,m), 7.83(2H,d,J=6.5 Hz), 8.30(2H,d,J=6.5 Hz), 8.48(1H,s) X-ray diffraction pattern:

The X-ray diffraction pattern shown in the following Table was obtained by using copper as cathode and λ=1.54060, 1.54439 A passed through a nickel filter (power source: 40 kV, 20 mA). The interplanar spacing is given as "d" and the relative strength is given as "I/Imax" in the Table.

| d | I/Imax (%) |
| --- | --- |
| 34.6865 | 8.31 |
| 12.3019 | 19.49 |
| 8.6232 | 27.30 |
| 8.2423 | 22.80 |
| 7.1902 | 8.31 |
| 5.8937 | 48.12 |
| 5.8176 | 51.94 |
| 5.3131 | 26.37 |
| 5.1513 | 20.29 |
| 4.5976 | 17.93 |
| 4.4158 | 44.44 |
| 4.2510 | 18.70 |
| 4.0580 | 39.77 |
| 3.9269 | 9.94 |
| 3.7348 | 100.00 |
| 3.4606 | 45.65 |
| 3.2964 | 35.35 |
| 3.0574 | 9.94 |
| 2.9025 | 16.44 |
| 2.8533 | 11.11 |
| 2.6699 | 27.30 |
| 2.6112 | 15.01 |
| 2.5393 | 15.71 |
| 2.4356 | 22.80 |

EXAMPLE 3

Crystal of 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl[-3-cephem-4-carboxylic acid formic acid solvate 1.0 g of disodium 7-[(Z)-2-(2-aminothiazol-4-yl)-2-[[(S)-α-carboxylato-3,4-dihydroxybenzyl]oxyimino]acetamido]-3-[(1-carboxylatomethyl-4-pyridinio)thiomethyl]-3-cephem-4-carboxylate was dissolved in 5 ml of formic acid and 6 ml of water was added thereto. After stirring at room temperature for 10 minutes, a seed crystal was added to the solution and stirred for 1 hour. 4 ml of water was further added thereto and stirred at room temperature for 1 hour. The precipitated crystal was collected and washed with water (3.5 ml×2) and acetone (3.5 ml×2), followed by air-drying at room temperature over one night, whereby 840 mg of the above-identified crystal was obtained. The melting point, IR, NMR and X-ray diffraction pattern of the compound were identical to those of the compound obtained in Example 2.

EXAMPLE 4

Crystal of 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid hydrate 210 mg of 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid formic acid solvate was suspended in 6 ml of water and stirred at room temperature for 15 hours. The crystal was collected by filtration and washed with 1.4 ml of water and 1.4 ml of acetone, followed by air-drying at room temperature for 15 hours, whereby 196 mg of the above-identified crystal was obtained.

Melting point: 202° C. (decomposition) IR(KBr)cm$^1$: 3400, 1770, 1630, 1530, 1380, 1100 NMR (D$_2$O, NaHCO$_3$) δ: 3.22 and 3.56(2H,ABq,J=18 Hz), 4.20 and 4.34(2H,ABq,J=14 Hz), 5.02(2H,s), 5.08(1H,d,J=4.5 Hz), 5.44(1H,s), 5.69(1H,d,J=4.5 Hz), 6.8–7.1(4H,m), 7.83(2H,d,J=6.5 Hz), 8.30(2H,d,J=6.5 Hz)

X-ray diffraction pattern:

The measurement conditions of the X-ray diffraction pattern shown in the following Table were the same as in Example 2.

| d | I/Imax (%) |
| --- | --- |
| 8.4485 | 16.66 |
| 7.9826 | 14.25 |
| 7.1454 | 10.66 |
| 5.5764 | 52.49 |
| 5.0911 | 16.66 |
| 4.7685 | 51.02 |
| 4.5325 | 26.03 |
| 4.2485 | 57.02 |
| 4.0856 | 100.00 |
| 3.9265 | 28.15 |
| 3.8142 | 21.08 |
| 3.7310 | 27.08 |
| 3.5405 | 29.25 |
| 3.4079 | 17.50 |
| 3.0914 | 29.25 |
| 3.0083 | 17.50 |
| 2.7859 | 16.66 |
| 2.4961 | 14.25 |

EXAMPLE 5

Crystal of 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid hydrate 8.90 g of disodium 7-[(Z)-2-(2-aminothiazol-4-yl)-2-[[(S)-α-carboxylato-3,4-dihydroxybenzyl]oxyimino]acetamido]-3-[(1-carboxylatomethyl-4-pyridinio)thiomethyl]-3-cephem-4-carboxylate was dissolved in 35.6 ml of formic acid, and 17.8 ml of water and 450 mg of active carbon were added to the reaction solution, followed by stirring at room temperature for 1 hour. An insoluble substance was removed by filtration and washed with a mixture of 8.9 ml of formic acid and 4.5 ml of water. The filtrate and the wash liquid were combined. After adding 22.3 ml of water to the solution, a seed crystal was added and stirred at room temperature for 1.5 hours. Then, 17.8 ml of water was added and stirred at room temperature for 1 hour, and 26.7 ml of water was further added thereto and stirred for 1 hour. The precipitated crystal was collected and washed with 17.8 ml of a solution mixture of formic acid-water (2:1) and 17.8 ml of water. The crystal thus obtained, as it was in a wet state, was suspended in 180 ml of water and stirred at room temperature for 4 hours. The crystal was collected by filtration and washed with water (17.8 ml×2) and 17.8 ml of acetone, followed by air-drying at room temperature for 15 hours, thereby 6.87 g of the above-identified crystal was obtained. The melting point, IR, NMR and X-ray diffraction pattern of the compound were identical to those of the compound obtained in Example 4.

EXAMPLE 6

Crystal of-7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid hydrate 40.0 g of disodium 7-[(Z)-2-(2-aminothiazol-4-yl)-2-[[(S)-α-carboxylato-3,4-dihydroxybenzyl]oxyimino]acetamido]-3-[(1-carboxylatomethyl-4-pyridinio)thiomethyl]-3-cephem-4-carboxylate was dissolved in a solution mixture of 160 ml of formic acid and 80 ml of water and 2 g of active carbon were added thereto followed by stirring at room temperature for 1 hour. An insoluble substance was removed by filtration and washed with solution mixture of formic acid-water (2:1). The filtrate and the wash liquid were combined. After adding 100 ml of water and a seed crystal thereto, the solution was stirred at room temperature for 1 hour. Further, water was added for 1-hour interval in an amount of 40 ml, 160 ml and 80 ml, respectively and stirred at the same temperature for 3 hours. The precipitated crystal was collected and washed with 80 ml of a solution mixture of formic acid-water (2:1) and 80 ml of water. The crystal thus obtained, as it was in the wet state, was suspended in 750 ml of water and stirred at room temperature for 15 hours. The crystal was collected by filtration and washed with 80 ml of water and 80 ml of acetone followed by air-drying at room temperature for 15 hours, whereby the above-identified crystal was obtained. The melting point, IR, NMR and X-ray diffraction pattern of the compound were identical to those of the compound obtained in Example 4.

REFERENCE EXAMPLE 1

3,4-(methylenedioxy)mandelic acid 42.4g (1 mol) of lithium chloride and 140.3 g (2.5 mol) of potassium hydroxide were dissolved in 500 ml of ice water, and then, 10 g of a 90% trioctylmethylammonium chloride aqueous solution was added thereto. A solution prepared by dissolving 75 g (0.5 mol) of piperonal and bromoform (containing 13 v/v % ethanol, about 0.63 mol) in 500 ml of dioxane was dropwise added to the solution at a temperature of at most 5° C., and then, the mixture was stirred at the same temperature for 24 hours. The reaction mixture was adjusted to pH 1.5 with 130 ml of 6N hydrochloric acid and extracted with 500 ml of ethyl acetate. 500 ml of water was added to the organic layer, adjusted to pH 8.0 with potassium carbonate powder, and the aqueous layer was separated. 130 ml of 6N hydrochloric acid was added to the aqueous layer to adjust pH 1.5 and then extracted with 500 ml of ethyl acetate. The organic layer was dried over anhydrous magnesium sulfate and then concentrated under reduced pressure. A crystalline residue was collected by filtration, washed with methylene chloride and diethyl ether and dried under reduced pressure to obtain 55.5 g (yield: 57%) of the above identified compound as the slightly yellow powder.

IR(KBr)cm$^{-1}$: 3450, 3410, 1720, 1500, 1485, 1440, 1250, 1205, 1065, 1045, 930, 810 NMR (DMSO-d$_6$) δ: 4.94(1H,s), 5,98(2H,s), 6.87(2H,s), 6.93(1H,s)

REFERENCE EXAMPLE 2

2-chloro-2-(3,4-dioxycarbonylphenyl)acetic acid

To a mixture prepared by adding 930.8 g (4.47 mol) of phosphorus pentachloride to 2.1 l of benzene, 175.3 g (0.894 mol) of the compound obtained in Reference Example 1 was added at a temperature of at most 10° C. over a period of 30 minutes. Further, the mixture was stirred at the same temperature for 30 minutes and then stirred at a temperature of 70° C. for one hour and under refluxing with heating for 20 hours. The reaction mixture was added to 8 l of ice water, then 4 l of ethyl acetate was added thereto, and the mixture was stirred for one hour. The organic layer was separated and washed with 4 l of water and with a mixed solution of 4 l of water and 140 ml of a saturated sodium hydrogencarbonate aqueous solution and then dried over anhydrous magnesium sulfate. The organic layer was concentrated under reduced pressure to obtain an oily residue, and seed crystals of the desired product were added thereto to conduct the crystallization. The crystals thereby formed were collected by filtration, washed with hexane and dried under reduced pressure to obtain 154.2 g (yield: 76%) of the above identified compound as crystalline powder.

IR(KBr)cm$^{-1}$: 3080, 3050, 2980, 1840, 1820, 1710, 1490, 1440, 1260, 1240, 1190, 1150, 1030, 970, 920, 820, 750, 700, 690 NMR (DMSO-$d_6$) δ: 5.83(1H,s), 7.46(2H,s), 7.59(1H,s)

REFERENCE EXAMPLE 3

2-(3,4-dioxycarbonylphenyl)-2-(phthalimidoxy)acetic acid

A solution prepared by dissolving 6.52 g (0.04 mol) of N-hydroxyphthalimide and 11.16 ml (0.08 mol) of triethylamine in 20 ml of acetonitrile was dropwise added to a solution prepared by dissolving 9.14 g (0.04 mol) of the compound obtained in Reference Example 2 in 50 ml of acetonitrile at a temperature of from −5° to 0° C. over a period of 25 minutes. The mixture was stirred at a temperature of at most 5° C. and at room temperature for one hour respectively, and then cooled to 0° C. A mixed solution of 3.5 ml of concentrated hydrochloric acid and 50 ml of water was added thereto, and 50 ml of water was further dropwise added thereto. An oily substance separated during the dropwise addition and gradually crystallized. After stirring at a temperature of at most 5° C. for 20 hours, the filtration was conducted. The crystals thereby obtained were washed twice with 40 ml of water and with 40 ml of a mixed solution of ethyl acetate/hexane (½) and then dried under reduced pressure to obtain 9.57 g (yield: 67%) of the above identified compound as crystals.

Melting point: 184°–185° C. IR(KBr)cm$^{-1}$: 3240, 1870, 1850, 1745, 1725, 1495, 1450, 1360, 1270, 1180, 960, 870, 700 NMR (DMSO-$d_6$) δ: 5.82(1H,s), 7.49(2H,s), 7.66(1H,s), 7.82(4H,s)

REFERENCE EXAMPLE 4

(R)-(+)-α-methylbenzylammonium (S)-2-(3,4-dioxycarbonylphenyl)-2-(phthalimidoxy)acetate To a solution prepared by dissolving 8.93 g (0.025 mol) of the compound obtained in Reference Example 3 in 250 ml of acetone, a solution prepared by dissolving 3.23 ml (0.025 mol) of R-(+)-α-methylbenzylamine in 20 ml of acetone was added under a nitrogen stream under vigorously stirring. After stirring for 30 minutes, deposited precipitates were collected by filtration under nitrogen stream, washed with a large amount of acetone and then dried under reduced pressure to obtain 3.97 g (yield: 33%) of the above identified compound as powder.

Melting point: 122°–125° C. Angle of rotation: [α]$_D^{21}$+284.6° (c 1.07, ethanol) IR(KBr)cm$^{-1}$: 3430, 2950, 1840, 1735, 1595, 1495, 1445, 1360, 1240, 1185, 960, 875, 770, 700 NMR (DMSO-$d_6$) δ: 1.47(3H,d,J=6 Hz), 4.36(1H,q,J=6 Hz), 5.48(1H,S), 7.41(5H,S), 7.48(2H,S), 7.63(1H,S), 7.83(4H,S)

REFERENCE EXAMPLE 5

Benzhydryl (S)-2-(3,4-dioxycarbonylphenyl)-2-(phthalimidoxy)acetate

To a suspension of 3.46 g (7.23 mmol) of the compound obtained in Reference Example 4 in 35 ml of methylene chloride, 6.9 ml of 2N hydrochloric acid was added at room temperature, and then a solution of 1.40 g (7.23 mmol) of diphenyldiazomethane in 8 ml of methylene chloride was added thereto. The mixture was stirred for 30 minutes. Further, 0.2 g (1.03 mmol) of diphenyldiazomethane was added thereto, and the mixture was stirred for 30 minutes. Then, the organic layer was separated and added to 100 ml of ethanol. Most of methylene chloride was distilled off under reduced pressure, and the residue was stirred under cooling with ice for one hour. Precipitated crystals were collected by filtration, washed three times with 10 ml of ethanol and then dried under reduced pressure to obtain 3.15 g (yield: 84%) of the above identified compound as crystalline powder.

Melting point: 134°–135° C. Angle of rotation: [α]$_D^{21}$+119.0° (c 1.18, ethyl acetate) IR (KBr)cm$^{-1}$: 1830, 1750, 1730, 1495, 1450, 1355, 1260, 1240, 1170, 1130, 960, 935, 700 NMR (DMSO-$d_6$) δ: 6.19(1H,S), 6.92(1H,S), 7.2–7.4(10H,m), 7.52(2H,s), 7.67(1H,s), 7.82(4H,s)

REFERENCE EXAMPLE 6

Benzhydryl (S)-2-aminoxy-2-(3,4-dihydroxyphenyl)acetate 63.3 g (0,121 mol) of the compound obtained by the method of Reference Example 5 was dissolved in 4.3 l of methanol, and 67 ml of 1N hydrochloric acid was added thereto. The mixture was stirred at 40° C. for 5 hours. Methanol was distilled off under reduced pressure, and the residue was dissolved in 500 ml of methylene chloride and washed twice with 250 ml of water. The methylene chloride layer was dried over anhydrous magnesium sulfate and then concentrated under reduced pressure to dryness. The residue was dissolved in 1.9 l of methylene chloride and cooled to −50° C. Then, 16.6 ml of hydrazine hydrate was added thereto, and the mixture was gradually warmed to room temperature and stirred for 5 hours. Insolubles were removed by filtration and washed with methylene chloride. The filtrate and the washing solution were put together, washed with 1.2 l of a 5% citric acid aqueous solution and twice with 1 l of water, dried over anhydrous magnesium sulfate and then concentrated under reduced pressure. Precipitated crystals were collected by filtration, washed with hexane and then dried under reduced pressure to obtain 38.3 g (yield: 87%) of the above identified compound as crystalline powder.

Angle of rotation: $[\alpha]_D^{21} +22.70°$ (c 1.03, ethanol)
IR(KBr)cm$^{-1}$: 3525, 3320, 3280, 1735, 1600, 1520, 1445, 1285, 1250, 1200, 1045, 750, 695, 600 NMR (DMSO-d$_6$) δ: 5.02(1H,S), 6.28(2H,br s), 6.68(2H,s), 6.79(2H,s), 7.1–7.4(10H,m), 8.93(2H,s)

REFERENCE EXAMPLE 7

(Z)-2-[[(S)-α-benzhydryloxycarbonyl-3,4-dihydroxybenzyl]oxyimino]-2-(2-tritylaminothiazol-4-yl)acetic acid A solution of 34.0 g (0.093 mol) of the compound obtained in Reference Example 6 in 440 ml of methanol was dropwise added to a solution of 38.6 g (0.093 mol) of (2-tritylaminothiazol-4-yl)glyoxylic acid in 120 ml of methanol under cooling with ice over a period of 5 minutes. The mixture was stirred at the same temperature for 30 minutes and then warmed to room temperature over a period of 1.5 hours. The reaction mixture was added to 900 ml of ice water and extracted with 1 l of ethyl acetate. The ethyl acetate layer was washed twice with 400 ml of a saturated sodium chloride aqueous solution and then dried over anhydrous magnesium sulfate. The solvent was distilled off under reduced pressure. Precipitated crystals were collected by filtration, washed with a mixed solution of ethyl acetate/hexane (½) and then dried under reduced pressure to obtain 53.0 g (yield: 75%) of the above identified compound as crystalline powder.

Angle of rotation: $[\alpha]_D^{21} +23.80°$ (C 1.02, methanol)
IR (KBr) cm$^{-1}$: 3380, 3050, 3025, 1735, 1590, 1525, 1490, 1445, 1250, 1180, 750, 700 NMR (DMSO-d$_6$) δ: 5.53(1H,s), 6.6–6.9(5H,m), 7.0–7.6(25H,m), 8.6–9.3(3H,br m)

REFERENCE EXAMPLE 8

(R)-2-(3,4-dioxycarbonylphenyl)-2-(phthalimidoxy)acetic acid

By using 164.3 g (0.46 mol) of the compound obtained in Reference Example 3, 4.6 l of acetone, 59.6 ml (0.46 mol) of R-(+)-α-methylbenzylamine and 360 ml of acetone, the treatment was conducted in accordance with the method of Reference Example 4 to obtain 91.5 g (yield: 42%) of powdery (R)-(+)-α-methylbenzylammonium (S)-2-(3,4-dioxycarbonylphenyl)-2-(phthalimidoxy)acetate. To the mother liquor, 300 ml of water and 100 ml of 6N hydrochloric acid were added, and then the mixture was extracted with 2 l of ethyl acetate. The ethyl acetate layer was washed twice with 400 ml of a saturated sodium chloride aqueous solution and then dried over anhydrous magnesium sulfate. The solvent was distilled off under reduced pressure. Precipitated crystals were collected by filtration, washed with ethyl acetate/hexane (½) and dried to obtain 49.0 g (yield: 30%) of the above identified compound.

REFERENCE EXAMPLE 9

Benzhydryl (R)-2-(3,4-dioxycarbonylphenyl)-2-(phthalimidoxy)acetate 49.0 g (0.138 mol) of the compound obtained in Reference Example 8 was suspended in a mixed solution of 900 ml of ethyl acetate and 200 ml of acetone, and 26.8 g (0.138 mol) of diphenyldiazomethane was added thereto at room temperature over a period of one hour and 40 minutes to obtain a solution. The solvent was distilled off under reduced pressure to obtain an oily substance, and 200 ml of ethanol was added thereto.

The mixture was stirred under cooling with ice for 2 hours. Precipitated crystals were collected by filtration, washed twice with 100 ml of ethanol and then dried to obtain 59.4 g (yield: 83%) of the above identified compound.

REFERENCE EXAMPLE 10

Benzhydryl (R)-2-aminoxy-2-(3,4-dihydroxyphenyl)acetate

By using 10.43 g (20 mmol) of the compound obtained in Reference Example 9, 700 ml of methanol, 10 ml of 1N hydrochloric acid, 300 ml and 320 ml of methylene chloride and 2.74 ml of hydrazine hydrate, the treatment was conducted in the same manner as in Reference Example 6 to obtain the oily above identified compound. The product was used to subsequent reactions without purification.

REFERENCE EXAMPLE 11

(Z)-2-[[(R)-α-benzhydryloxycarbonyl-3,4-dihydroxybenzyl]oxyimino]-2-(2-tritylaminothiazol-4-yl)acetic acid By using the oily substance obtained in Reference Example 10, 90 ml of methanol and 7.47 g (18 mmol) of (2-tritylaminothiazol-4-yl)glyoxylacetic acid, the treatment was conducted in the same manner as in Reference Example 7 to obtain 11.6 g (yield: calculated from the compound of Reference Example 9: 76%) of the above identified compound as crystalline powder.

Angle of rotation: $[\alpha]_D^{21} -18.9°$ (c 1.0, methanol)
IR(KBr)cm$^{-1}$: 3380, 3050, 3025, 1740, 1595, 1520, 1490, 1445, 1260, 1190, 750, 700

REFERENCE EXAMPLE 12

Preparation of 1-benzhydryloxycarbonylmethyl-4-pyridothione (A) 4 g (42.06 mmol) of 4-hydroxypyridine was dissolved in 80 ml of N,N-dimethylformamide, and 8.7 g (62.92 mmol) of potassium carbonate and 16.45 g (63 mmol) of benzhydryl 2-chloroacetate were added thereto. The mixture was stirred at 60° C. for 4 hours. 200 ml of ethyl acetate was added to the reaction solution. The ethyl acetate layer was washed with water and with a saturated sodium chloride aqueous solution, dried over anhydrous sodium sulfate and then treated with active carbon. The solvent was distilled off under reduced pressure, and the crystalline residue was washed with diethyl ether to obtain 9.8 g (yield: 73%) of 1-benzhydryloxycarbonylmethyl-4-pyridone.

IR(KBr)cm$^{-1}$: 1750, 1650, 1575, 1200, 700 NMR (CDCl$_3$) δ: 4.70(2H,s), 6.90(1H,s), 6.01–7.50(14H,m)

(B) 1.35 g (4.23 mmol) of the compound obtained in the above reaction (A) was dissolved in 27 ml of tetrahydrofuran, and 940 mg (4.23 mmol) of phosphorus pentasulfide was added thereto. The mixture was stirred at 60° C. for 3 hours. The solvent was distilled off under reduced pressure from the reaction solution, and 50 ml of ethyl acetate was added to the residue. The ethyl acetate solution was washed with a saturated sodium hydrogencarbonate aqueous solution and with a saturated sodium chloride aqueous solution and then dried over anhydrous sodium sulfate. The solvent was distilled off under reduced pressure, and the residue was subjected to silica gel column chromatography (chloroform/methanol=20/1) to obtain 730 mg (yield: 51.5%) of the above identified compound.

IR(KBr)cm$^{-1}$: 1750, 1620, 1470, 1220, 1190, 1120, 700 NMR (DMSO-d$_6$) δ: 6.16(2H,s), 6.90(1H,s), 7.18(2H,d,J=6 Hz), 7.38(10H,s), 7.57(2H,d,J=6 Hz)

REFERENCE EXAMPLE 13

Disodium 7-[(Z)-2-(2-aminothiazol-4-yl)-2-[[(R)-α-carboxylato-3,4-dihydroxybenzyl]oxyimino]acetamido]-3-[(1-carboxylatomethyl-4-pyridinio)thiomethyl]-3-cephem-4-carboxylate (A) By using 4.57 g (6 mmol) of (Z)-2-[[(R)-α-benzhydryloxycarbonyl-3,4-dihydroxybenzyl]oxyimino]-2-(2-tritylaminothiazol-4-yl)acetic acid, 2.03 g (5 mmol) of p-methoxybenzyl 7-amino-3-chloromethyl-3-cephem-4-carboxylate, 1.39 ml (10 mmol) and 0.84 ml (6 mmol) of triethylamine and 0.75 ml (8 mmol) of phosphorus oxychloride, the treatment was conducted in the same manner as in Example 1 (A) to obtain 5.60 g (yield: 56%) of p-methoxybenzyl 7-[(Z)-2-[[(R)-α-benzhydryloxycarbonyl-3,4-dihydroxybenzyl]oxyimino]-2-(tritylaminothiazol-4-yl)acetamido]-3-chloromethyl-3-cephem-4-carboxylate as a foam-like solid.

(B) By using 5.60 g (5 mmol) of the compound obtained in the above reaction (A), 50 ml of N,N-dimethylformamide, 3.7 g (22 mmol) of potassium iodide and 1.68 g (5 mmol) of 1-benzhydryloxycarbonylmethyl-4-pyridothione, the treatment was conducted in the same manner as in Example 1 (B) to obtain 7.70 g (yield: 100%) of p-methoxybenzyl 7-[(Z)-2-[[(R)-α-benzhydryloxycarbonyl-3,4-dihydroxybenzyl]oxyimino]-2-(tritylaminothiazol-4-yl)acetamido]-3-[(1-benzhydryloxycarbonylmethyl-4-pyridinio)thiomethyl]-3-cephem-4-carboxylate iodide as a foam-like solid.

(C) By using 7.70 g (5 mmol) of the compound obtained in the above reaction (B), 25 ml of methylene chloride, 4.9 ml of anisole and 52 ml of trifluoroacetic acid, the treatment was conducted in the same manner as in Example 1 (C) to obtain 1.66 g (yield: 45%) of the above identified compound.

IR(KBr)cm$^{-1}$: 3420, 1770, 1635, 1600, 1530, 1380, 1290, 1110, 740 NMR (D$_2$O) δ: 3.14 and 3.52(2H,ABq,J=18 Hz), 4.09 and 4.42(2H,ABq,J=13 Hz), 5.02(3H,br s), 5.42(1H,s), 5.66(1H,d,J=4.5 Hz), 6.85(1H,d,J=8 Hz), 6.93(1H,d,J=8 Hz), 6.98(1H,s), 7.03(1H,s), 7.86(2H,d,J=7 Hz), 8.32(2H,d,J=7 Hz) HPLC: Column: YMC®-Pack A-302 C$_{18}$5μ, 4.6φ×150 mm Mobile phase: 0.01M phosphoric acid aqueous solution/methanol (80/20) Flow rate: 1.0 ml/min. Temperature: 40° C. Detection: 280 nm Retention time: 6.21 min.

INDUSTRIAL APPLICABILITY

The compound of the present invention is a novel optically active amorphous or crystalline compound and has strong antibacterial activities and a widely well-balanced excellent antibacterial spectrum against sensitive or tolerant Gram-positive bacteria and Gram-negative bacteria, particularly glucose non-fermentative Gram-negative rods containing *Pseudomonas aeruginosa*. Further, it is excellent in the stability against β-lactamase. Particularly, the crystalline compound is more excellent in the stability and useful as an antibacterial agent.

What is claimed is:

1. A crystalline optically active compound of S-configuration of the structural formula I:

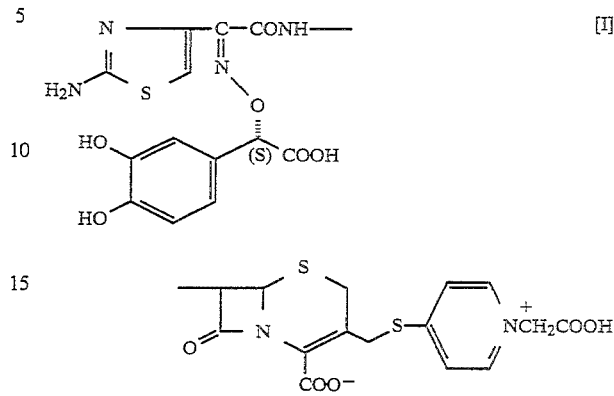

or its pharmaceutically acceptable salt or ester.

2. The optionally active compound according to claim 1, wherein its X-ray diffraction pattern is:

| d | I/Imax (%) |
|---|---|
| 34.6865 | 8.31 |
| 12.3019 | 19.49 |
| 8.6232 | 27.30 |
| 8.2423 | 22.80 |
| 7.1902 | 8.31 |
| 5.8937 | 48.12 |
| 5.8176 | 51.94 |
| 5.3131 | 26.37 |
| 5.1513 | 20.29 |
| 4.5976 | 17.93 |
| 4.4158 | 44.44 |
| 4.2510 | 18.70 |
| 4.0580 | 39.77 |
| 3.9269 | 9.94 |
| 3.7348 | 100.00 |
| 3.4606 | 45.65 |
| 3.2964 | 35.35 |
| 3.0574 | 9.94 |
| 2.9025 | 16.44 |
| 2.8533 | 11.11 |
| 2.6699 | 27.30 |
| 2.6112 | 15.01 |
| 2.5393 | 15.71 |
| 2.4356 | 22.80 |

3. A crystalline optically active compound of S-configuration which is 7-[(Z)-2-(2-aminothiazol-4-yl)-2-[[(S)-α-carboxy-3,4-dihydroxybenzyl]oxyimino]acetamido]-3-[(1-carboxylatomethyl-4-pyridinio)thiomethyl]-3-cephem-4-carboxylic acid, its pharmaceutically acceptable salt or ester, or its solvate.

4. The compound according to claim 3, which is a crystalline formic acid solvate.

5. The compound according to claim 3, which is a crystalline hydrate.

6. An antibacterial composition comprising an effective amount of the compound of claim 3 in admixture with a pharmaceutically acceptable, non-toxic carrier or excipient.

7. A method for the treatment of an infectious disease in a subject needing such treatment, which comprises administering an effective amount of the compound of claim 3 to the subject.

* * * * *

UNITED STATES PATENT AND TRADEMARK OFFICE
CERTIFICATE OF CORRECTION

PATENT NO. : 5,407,930
DATED : April 18, 1995
INVENTOR(S) : Susumu NAKAGAWA, et al.

It is certified that error appears in the above-indentified patent and that said Letters Patent is hereby corrected as shown below:

In Column 1, Line 14 of the Letters Patent, the second PCT Number should read:

--PCT/JP89/01155--

Signed and Sealed this

Fourth Day of July, 1995

Attest:

BRUCE LEHMAN

Attesting Officer     Commissioner of Patents and Trademarks